United States Patent
Sandvik et al.

(10) Patent No.: US 8,505,303 B2
(45) Date of Patent: Aug. 13, 2013

(54) IMPURITY DETECTION IN COMBUSTOR SYSTEMS

(75) Inventors: Peter Micah Sandvik, Niskayuna, NY (US); Richard Dale Slates, Minden, NV (US); Alexey Vasily Vert, Schenectady, NY (US); Samer Aljabari, Amman (JO)

(73) Assignee: General Electric Company, Niskayuna, NY (US)

( * ) Notice: Subject to any disclaimer, the term of this patent is extended or adjusted under 35 U.S.C. 154(b) by 914 days.

(21) Appl. No.: 12/635,742

(22) Filed: Dec. 11, 2009

(65) Prior Publication Data
US 2011/0138813 A1 Jun. 16, 2011

(51) Int. Cl.
*F02C 7/22* (2006.01)

(52) U.S. Cl.
USPC ......... 60/740; 60/39.821; 60/39.827; 60/773; 356/315; 356/316; 422/82.09; 73/23.31; 73/23.33

(58) Field of Classification Search
USPC ................ 60/740, 772, 773, 39.821, 39.827; 356/315, 316; 422/82.09; 702/22, 24, 25, 702/27; 73/23.31–23.33
See application file for complete search history.

(56) References Cited

U.S. PATENT DOCUMENTS

| | | | |
|---|---|---|---|
| 3,080,708 A * | 3/1963 | Carr | 60/208 |
| 4,616,137 A | 10/1986 | Goff et al. | |
| 4,914,349 A * | 4/1990 | Matsui et al. | 313/524 |
| 4,922,714 A | 5/1990 | Grob et al. | |
| 5,152,963 A | 10/1992 | Wreyford | |
| 6,135,760 A | 10/2000 | Cusack et al. | |
| 6,268,913 B1 * | 7/2001 | Rising | 356/326 |
| 6,800,870 B2 * | 10/2004 | Sayag | 250/584 |
| 6,978,074 B2 * | 12/2005 | Shu et al. | 385/137 |
| 7,112,796 B2 | 9/2006 | Brown et al. | |
| 7,202,946 B2 * | 4/2007 | Powell et al. | 356/316 |
| 7,271,894 B2 * | 9/2007 | Devitt et al. | 356/241.1 |
| 7,334,413 B2 | 2/2008 | Myhre | |
| 7,907,272 B2 * | 3/2011 | Zelepouga et al. | 356/300 |
| 2002/0024672 A1 | 2/2002 | Shibamoto | |
| 2002/0137227 A1 * | 9/2002 | Weckstrom | 436/172 |
| 2004/0237505 A1 | 12/2004 | Leipertz | |
| 2008/0289342 A1 * | 11/2008 | Sappey et al. | 60/793 |
| 2009/0141349 A1 | 6/2009 | Myhre | |

FOREIGN PATENT DOCUMENTS

| | | |
|---|---|---|
| JP | 2000241249 A | 9/2000 |
| WO | 2004009390 A2 | 1/2004 |

OTHER PUBLICATIONS

Wehrmeyer, Joseph A., Emission Spectroscopy for Coal-Fired Cyclone Furnace Diagnostics, 2003, Society for Applied Spectroscopy, vol. 57, No. 8, pp. 1020-1026.*
Dale M. Brown et al; Silicon Carbide Photodiode Sensor for Combustion Control; IEEE Sensors Journal, vol. 5, No. 5, Oct. 2005; pp. 983-988.
Combustion optimization pushed forward by excimer LIF methods; A publication by Lambda Physik, Lambda Highlights No. 14; Dec. 1988; pp. 1-6.
Laser Spectroscopy in combustion research; © Rolf Bombach, Paul Scherrer Institute, Switzerland; Ercoftac Summer School, Mar. 2002, Zurich; pp. 1 - 27.

\* cited by examiner

*Primary Examiner* — Phutthiwat Wongwian
*Assistant Examiner* — Steven Sutherland
(74) *Attorney, Agent, or Firm* — Paul J. DiConza (57) ABSTRACT

The present invention discloses a combustor system and method of measuring impurities in the combustion system. The combustion system includes an up-stream fuel injection point; a down-stream turbine combustor; a flame zone in the turbine combustor comprising a plurality of axial sub-zones; an optical port assembly configured to obtain a non-axial, direct, optical view of at least one of the plurality of axial sub-zones, and an impurity detection system in optical communication with the optical port assembly.

25 Claims, 9 Drawing Sheets

IMPURITY DETECTION IN COMBUSTOR SYSTEMS

BACKGROUND

The invention generally relates to optical flame detection and particularly to determination of trace elements in liquid fuel flames of combustor systems through thermal atomic emission.

Gas turbines and burners can be configured to operate on different types of fuel including gas and liquid fuels. While gas fuels, such as natural gas and syngas, represent the majority of installations, the ability to operate using distillate or ash-bearing fuels of varying quality is an important enabler for the gas turbine product line. One major operational difficulty with the use of low-grade liquid fuels is the presence of trace-level metal elements in the fuel that can cause adverse effects on turbine materials, such as hot gas path corrosion and barrier coating degradation. These contaminants, if present, may burn and form reactants that disadvantageously coat the inside of the chamber (combustor) walls, in some cases clogging air flows and prohibiting the system from running optimally. Concentrations on the order of even 1 part per million by mass of some metallic elements in liquid fuel are known to be harmful in this regard. Further, fuel quality differs heavily in various parts of the world where combustor systems are located. Accordingly, it is highly desirable to detect and determine which (if any) contaminants may exist in a particular environment.

The usual defense against hot corrosion due to the presence of some of the metal elements, such as vanadium, is the addition of corrosion inhibitors to the fuel. The concentration of corrosion inhibitors is generally adjusted as a function of the level of metal contaminants in the fuel. An overcompensation of corrosive metal elements by inhibitor may result in the formation of additional ash deposits on the turbine components. Therefore, it is desirable to continuously monitor the levels of corrosive metal elements as well as the corrosion inhibitors in the fuel at the point of use.

Although there are some currently known methods and systems to provide impurity or contamination detection in the liquid fuels, disadvantages exist regarding the complexity and cost of multiple detector systems. Accordingly, there remains a need in the art for systems and methods for measurement of impurities that provide accurate measurements in a more efficient manner.

BRIEF DESCRIPTION

One embodiment of the present invention is a combustor system. The combustor system comprises an up-stream fuel injection point; a down-stream turbine combustor; a flame zone in the turbine combustor comprising a plurality of axial sub-zones; an optical port assembly configured to obtain a non-axial, direct, optical view of at least one of the plurality of axial sub-zones, and an impurity detection system in optical communication with the optical port assembly.

Another embodiment of the present invention is a combustor system. The combustion system comprises an up-stream fuel injection point; a down-stream turbine combustor; a flame zone in the turbine combustor comprising a plurality of axial sub-zones; an electrode assembly disposed at the vicinity of combustor system to excite the flame during operation; an optical port assembly configured to obtain a direct optical view of at least two of the plurality of axial sub-zones, and an impurity detection system in optical communication with the optical port assembly.

Another embodiment of the present invention is a combustor system. The combustion system comprises a fuel line; a slip-stream fuel line; an up-stream fuel injection point on the fuel line; a down-stream turbine combustor on the fuel line, and an inductively coupled plasma (ICP) analyzer disposed on the slip-stream fuel line for analyzing the impurities of fuels passing to the turbine combustor.

Yet another embodiment of the present invention is a method of analyzing and measuring specific impurities in a combustor system. The method comprises injecting a liquid fuel into a flame zone of the combustor system; generating a flame in the flame zone of the combustor system; increasing temperature of the flame by providing an external stimulation; coupling a direct emission signal of the flame from a plurality of axial subzones of the flame zone through an optical port assembly to a detector system, and analyzing the emission signal from the plurality of axial subzones to detect an impurity species present in the liquid fuel.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The systems and method described herein include embodiments that relate to impurity detection in a combustor system. Suitable combustion devices may include, for example, furnaces, ovens, and engines, such as gas turbine engines.

In the following specification and the claims that follow, the singular forms "a", "an" and "the" include plural referents unless the context clearly dictates otherwise.

The determination of trace elements in liquid fuel flames through thermal atomic emission (flame photometry) is an attractive concept for the monitoring of fuel quality for gas turbine applications. Flame photometry is passive, requiring only optical access to the combustion zone, and requires no incident radiation or external energy input, relying on combustion processes to provide the energy needed to excite analytes.

Monitoring the combustion flame cell by an optical spectrophotometer can enable the monitoring of potentially harmful contaminants burning in the combustion cells. The use of hydrocarbon fuels such as diesel as both the fuel and analyte matrix and using flame photometry for the identification and quantification of transition metals is largely unexplored. For impurity identification, transition metal elements give off characteristic light having spectral emission lines of known wavelength. This emission is mainly from electron energy level transitions that are determined by the atomic properties of the respective elements. These spectral emission lines, when monitored with the spectrophotometer, may potentially allow for a warning condition at which time, the fuel source could be treated appropriately.

The impurities that may be monitored in a combustor engine include, for example, sodium (Na), potassium (K), lithium (Li), vanadium (V), lead (Pb), calcium (Ca), hydrogen (H), and carbon (C). In one embodiment, the maximum concentration allowed for any of these elements is about 0.2 parts-per-million (ppm). In particular embodiments, this maximum concentration is about 0.1 ppm.

Some of the impurities also have associated spectroscopic absorption lines that are characteristic of associated molecules. These may be difficult to detect via optical absorption due to complexity of integration of the measurement setup with the combustion equipment. Therefore, collecting emission spectra directly from the combustion process is a simpler approach to detect the impurities compared to an absorption-based detection.

Figure 1:
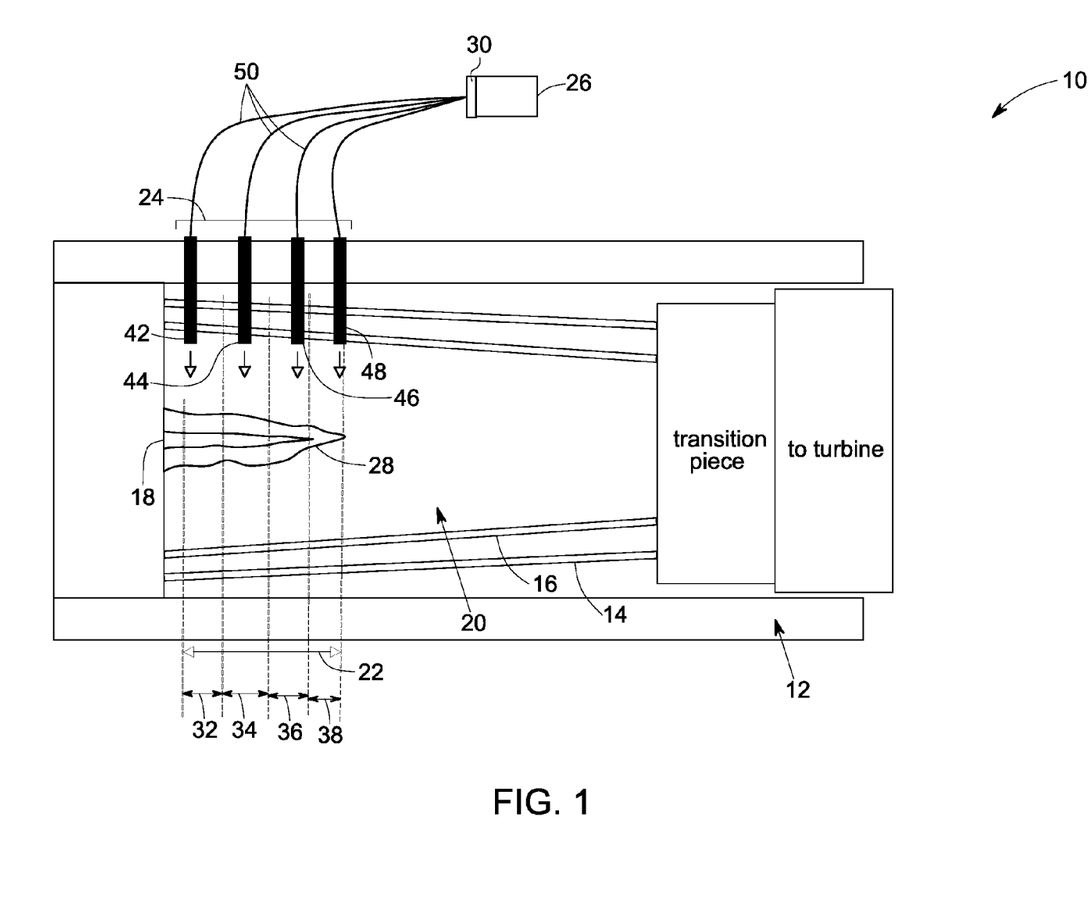
FIG. 1 is a schematic representation of a combustor system in accordance with one embodiment of the invention.

Embodiments of the present invention provide a combustor system and method of analyzing and measuring specific impurities in a combustor system. The combustor system may be gas-fueled or liquid-fueled. FIG. 1 depicts a combustor system 10 in accordance to an embodiment of the present invention. The combustor system 10 comprises a pressure boundary 12, reverse flow sleeve 14, an inner liner 16, an up-stream fuel injection point 18, a down-stream turbine combustor 20, a flame zone 22, an optical port assembly 24, and an impurity detection system 26. A flame zone 22 as used herein is a portion of the combustor system 10 where a flame 28 is supposed to exist when the system is in operation. The flame zone 22 in the combustor system 10 can be divided into a plurality of axial sub-zones. Axial sub-zones as used herein are the different zones defined by their varying temperature profiles. In one embodiment, the flame zone comprises a flame of temperature increasing from the fuel injection point in the nozzle end along the axis of the flame zone 22 during operation of combustor system.

For example, if the flame starts from the nozzle end and extends toward the turbine as shown in FIG. 1, then the flame zone 22 will be the zone where the flame is expected to be present at the time of operation. The nozzle-edge zone 32, mid flame zone 34, tip of the flame zone 36, and downstream zone 38 are different axial sub zones of the flame zone 22. In one embodiment, the nozzle-edge zone 32 has a lower temperature relative to the mid flame zone 34 and the temperature further increases in the tip of the flame zone 36, and then increases even further in the downstream zone 38.

An optical port assembly 24 as used herein may comprise a plurality of optical ports 42, 44, 46, 48 directed at one or more parts of the combustion zone. In one embodiment, the optical port assembly 24 is configured to obtain a non-axial, direct, optical view of at least one of the plurality of axial sub-zones. A non-axial view as used herein means that the view of the flame is not through the nozzle of the combustor. A direct optical view as used herein is a view of the flame without any solid intervening material. To achieve this, in one embodiment, optical ports 42, 44, 46, 48 penetrate through the pressure boundary 12 of the combustor system for a direct optical view of the flame 28.

In one embodiment, the plurality of optical ports 42, 44, 46, 48 are aligned to obtain different views of the flame 28 in the flame zone 22. In another embodiment, the plurality of optical ports is configured to obtain a direct view of at least two of the plurality of axial sub-zones. For example, there can be one or more optical ports having a perpendicular or radial view of any or each of the axial sub-zones of the flame zone 22, thereby providing radial viewing of different parts of the flame during operation of the combustor system 10. The thermal atomic spectra obtained from different axial sub-zones can differ for a particular impurity of a fuel source. This difference can depend on various factors affecting the emission spectra of any of the impurities singularly or in the presence of other impurities present. For example, a temperature difference in the two different axial sub-zones may allow different levels of manifestations of different peaks of the impurity. In another example, quenching of an emission peak of one impurity may depend on the strength of other impurity emission peaks in and around the wavelength of the initial impurity peak and strength of the emission peaks may depend on the temperature of the flame at the point of measurement.

There can also be one or more optical ports having oblique view of the flame enabling a better viewing angle of the flame thereby maximizing the viewed region size. In one embodiment, the monitoring system avoids interfering with gas flow from the gas inlets by designing the positioning of the optical ports with respect to gas inlets and outlets.

In one embodiment, the optical port assembly 24 is in optical communication with the impurity detection system 26. The optical communication in between the optical port assembly 24 and the impurity detection system 26 can happen either directly or through a set of optical fibers 50. In one embodiment, the impurity detection system is configured to detect impurity species comprising at least one element selected from the group consisting of sodium, potassium, calcium, lithium, magnesium, lead, and vanadium. In another embodiment, the impurity detection system is configured to detect impurity species comprising at least one oxide of the element selected from the group consisting of sodium, potassium, calcium, lithium, magnesium, lead, and vanadium.

In one embodiment, the impurity detection system 26 comprises a sensor assembly. The sensor assembly assists in sensing the thermal atomic emission spectra of the flame. The concentration of the impurities in the combustion system may be very low, for example, in the ppm levels. At this low level of impurity, the spectra collected will be very weak and difficult to detect. Therefore, a device with a very high gain is required to detect the thermal atomic emission. The sensor assembly of the present embodiment may comprise any one or multiple instruments that can detect the thermal atomic emission, and transmit for further analysis. Examples include a photospectrometer, photodiode, avalanche photodiode, and photomultiplier tube. In one embodiment, the sensor assembly comprises an avalanche photodiode (APD). In a further embodiment, the avalanche photodiode has a quantum efficiency greater than 10% at about 500 nm. In one embodiment, the sensor assembly comprises a photomultiplier tube (PMT) with a quantum efficiency greater than 10% at an incident wavelength of range of 300 to 700 nm. In some embodiments, the PMT is operated at gain levels of 1000 or greater.

In one embodiment, the impurity detection system 26 further comprises an analyzer assembly configured to analyze an output signal from the sensor assembly. The analyzer assembly can include an electronic signal processor that is adapted and configured to analyze and process real-time data received from or otherwise transmitted by the sensor assembly.

The thermal spectra collected may also contain background noise that reduces clarity of the thermal spectra of the intended impurities. An optical filter, such as a notch filter, for example, may prevent background radiation or irradiance from other materials from confounding the signals associated with the chosen impurity. Accordingly, in one embodiment, the impurity detector system 26 further comprises a filter assembly configured to selectively allow passage of a characteristic thermal atomic emission of an impurity existing in a fuel in the turbine combustor.

Optical filtering can be carried out using several approaches, including using a filter assembly comprising dielectric materials in thin film, thick film or bulk form, rare-earth doped glasses, or thick film polymers. The thin film filters of dielectric materials offer flexibility as they may be tailored optically to meet the user's demands. For example, a filter may be designed such that it allows only 580 to 600 nm radiation to pass through while blocking much of the visible and/or ultraviolet (UV) radiation. This, in principle, may facilitate a detector with a large wavelength range to observe a specific emission line such as sodium (at 590 nm). The filter assembly can be introduced in the combustor system in different ways. In one embodiment, the optical filters 30 are directly deposited on the impurity detection assembly 26 on the surface receiving the signal from the flame zone 22 or integrated within the optical ports.

In one embodiment, the filter assembly can be adjusted to have different pass band width to be applicable for the wavelength ranges of different impurities. In one embodiment, the pass band width of the filter assembly is less than 30 nm. In another embodiment, the pass band width of the filter assembly is less than 10 nm.

While the wavelength of emission of an impurity helps to identify the impurity element, intensity of the emitted radiation may be used to quantify the concentration of the impurity. In some cases, such as vanadium, for example, a typical gas turbine flame temperature is not high enough to produce efficient excitation of the atoms. The number of atoms existing in the excited state can be increased by increasing the flame temperature, such as through the creation of a plasma in the flame. Passage of electricity through the gap between electrodes located across the flame can provide the necessary energy to atomize the sample and excite the resulting atoms to higher electronic states.

Figure 2:
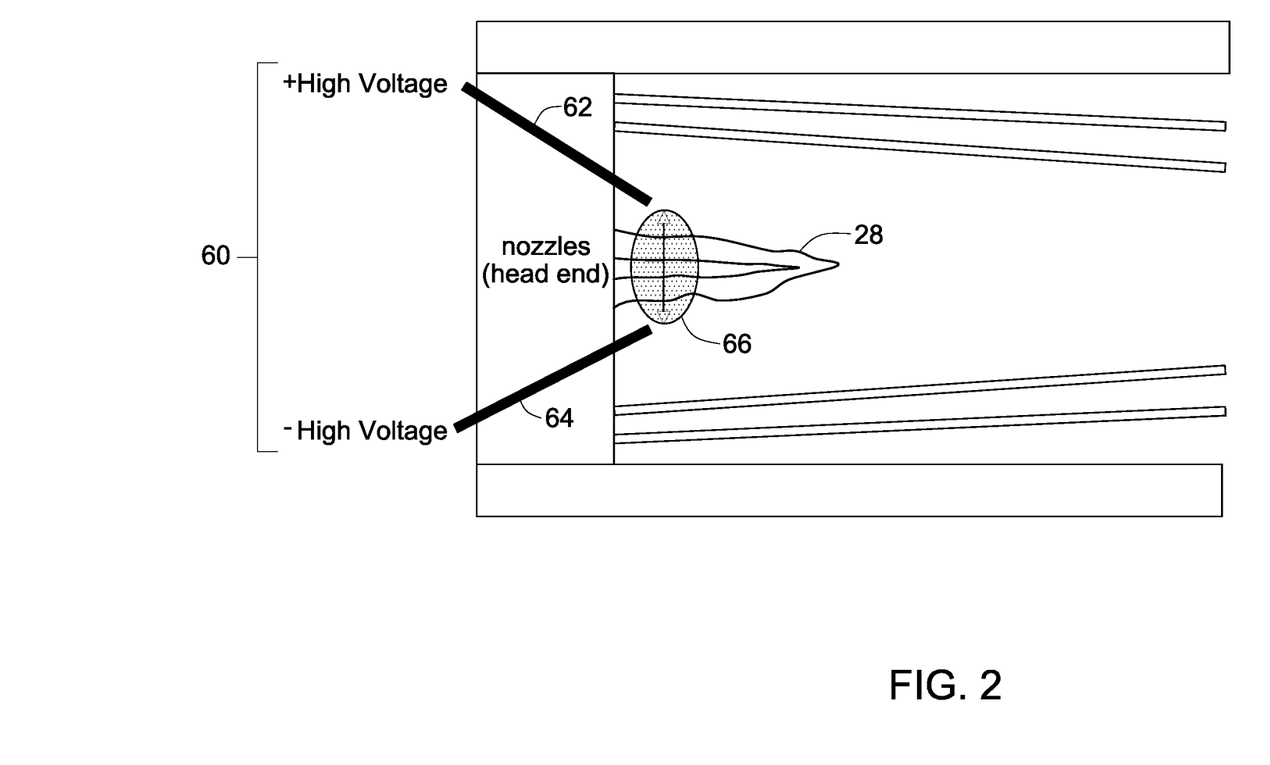
FIG. 2 is a schematic representation of a combustor system with an exciter assembly in accordance with one embodiment of the invention.

The combustor system 10, according to one embodiment, comprises an exciter assembly disposed to increase the temperature of the flame zone 22 as shown in FIG. 2. The exciter assembly of FIG. 2 comprises an electrode assembly 60 configured to produce electric discharge through the flame 28, thereby producing increased combustion temperature and generating plasma. The electrode assembly 60, when in operation, excites the flame. The electrode assembly 60 can comprise a pair of electrodes 62, 64 or can comprise multiple, non-connected electrode pairs. Plasma excitation of the flame 28, achieved by insertion of electrodes in the vicinity of the flame 28 and producing electric discharge or by electromagnetic induction, allows more efficient atomic excitation at higher temperatures.

In one embodiment, the electrode assembly 60 comprises a fast oscillating electromagnetic field to create a plasma 66 in the flame zone 22. In a further embodiment, plasma 66 is created by an RF coil. In another exemplary embodiment, an inductively coupled plasma (ICP) analyzer is used for analyzing the impurities of fuels passing to the turbine combustor. In yet another embodiment, multiple RF coils and electrodes are positioned around the flame 28 to shape electromagnetic field distribution for improved overlap of the electromagnetic energy with the flame 28.

Figure 3:
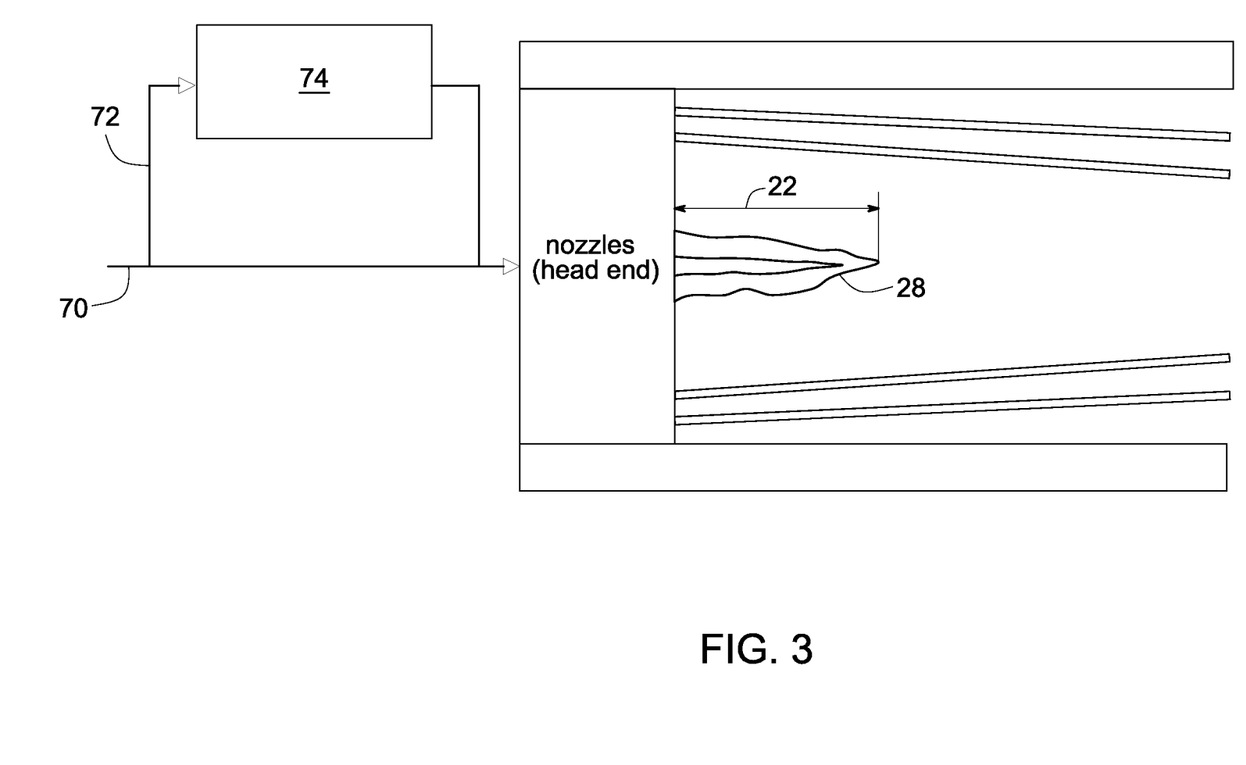
FIG. 3 is a schematic representation of a combustor system with an ICP analyzer in a slip-stream in accordance with one embodiment of the invention.

The analysis of the impurities in the fuel can happen either in a combustion chamber of the system or in a chamber to which a slip-stream of the fuel is fed as shown in FIG. 3. The slip-stream 72 can be taken from the main fuel line 70 entering the flame zone 22. The thermal atomic emission of the flame occurring in the fuel line or the slip-stream can be analyzed to obtain the identification and quantification of the impurities in the fuel. In one embodiment, an ICP analyzer 74 is disposed on the slip-stream fuel line for analyzing the impurities of fuels passing to the turbine combustor.

One embodiment includes a method of measuring and analyzing the impurities in fuel. In one embodiment, the specific impurities in a fuel are measured and analyzed by burning the fuel in a combustor system 10. In another embodiment, the fuel is burned in a burning zone created for the slip-stream of the fuel line. In an exemplary embodiment, the fuel is burned inside an ICP 74. Liquid fuel, for example, is injected into a flame zone 22 of the combustor system 10 through an up-stream fuel injection point. Direct emission signals of the flame generated in a plurality of axial subzones of the flame zone 22 is coupled to an impurity detection system 26 through an optical port assembly 24. The emission signals from the plurality of axial subzones are analyzed to detect an impurity species present in the liquid fuel. As disclosed in the earlier paragraphs, the temperature of the flame can be increased by providing an external stimulation to increase accuracy of the measurement. The impurity species detected by using this method comprises at least one element and/or oxides of the element selected from the group consisting of sodium, potassium, calcium, lithium, magnesium, lead, and vanadium. In one embodiment, the method of detecting impurity species includes comparison of different peak intensity bandwidths of the impurity species.

Example 1

Figure 4:
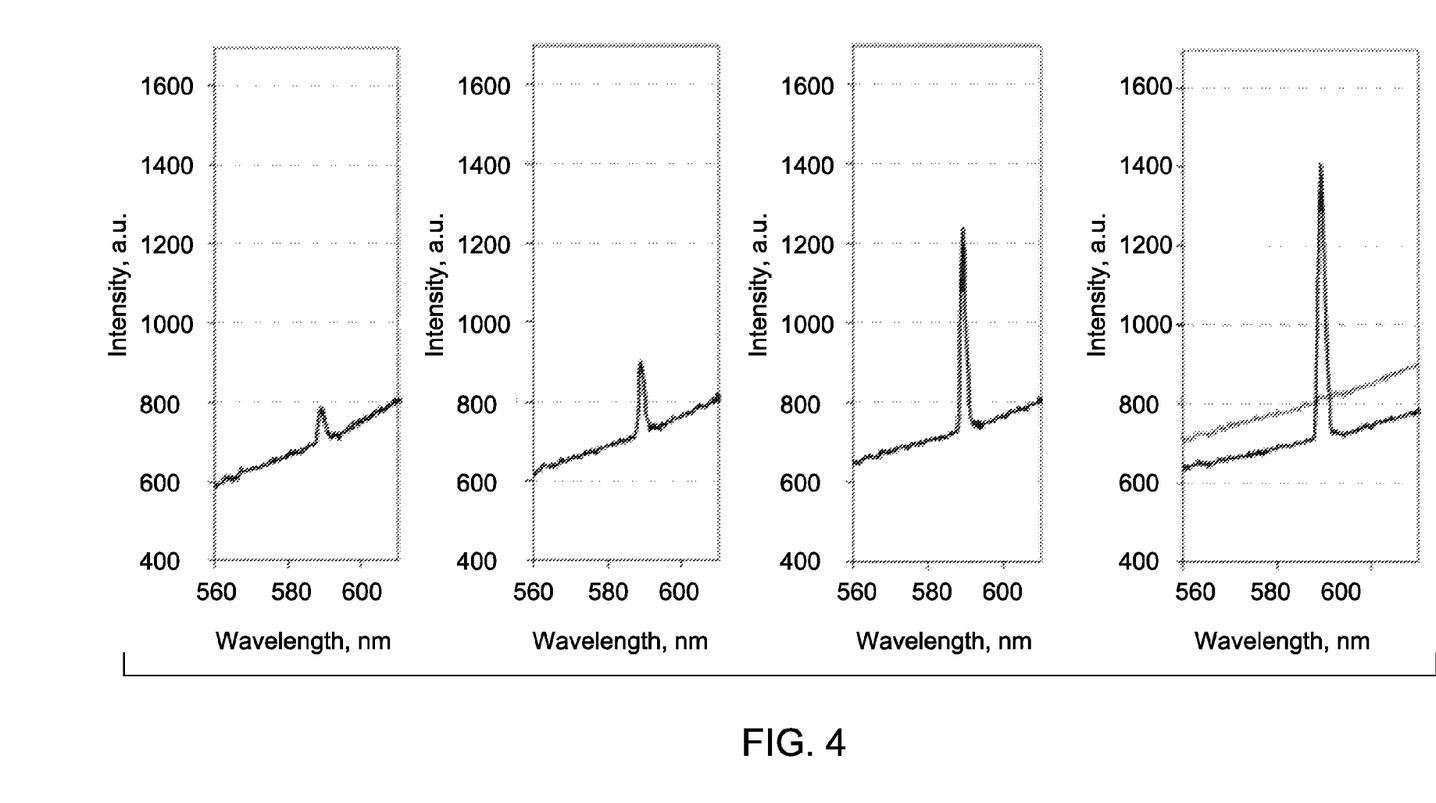
FIG. 4 is flame emission spectra of sodium in accordance with one embodiment of the invention.

A spray fuel flame combustion setup was used to characterize optical emission of burning jet fuel. Clean jet fuel was mixed with contaminated fuel using syringe pumps to produce different concentrations of contaminants. FIG. 4 shows relative intensity of a sodium emission line in the flame with different concentrations of sodium. The emission intensity was approximately proportional to the sodium concentration in the fuel. The concentration of sodium in percentage was determined relative to the maximum concentration achieved during the test.

Example 2

Figure 5:
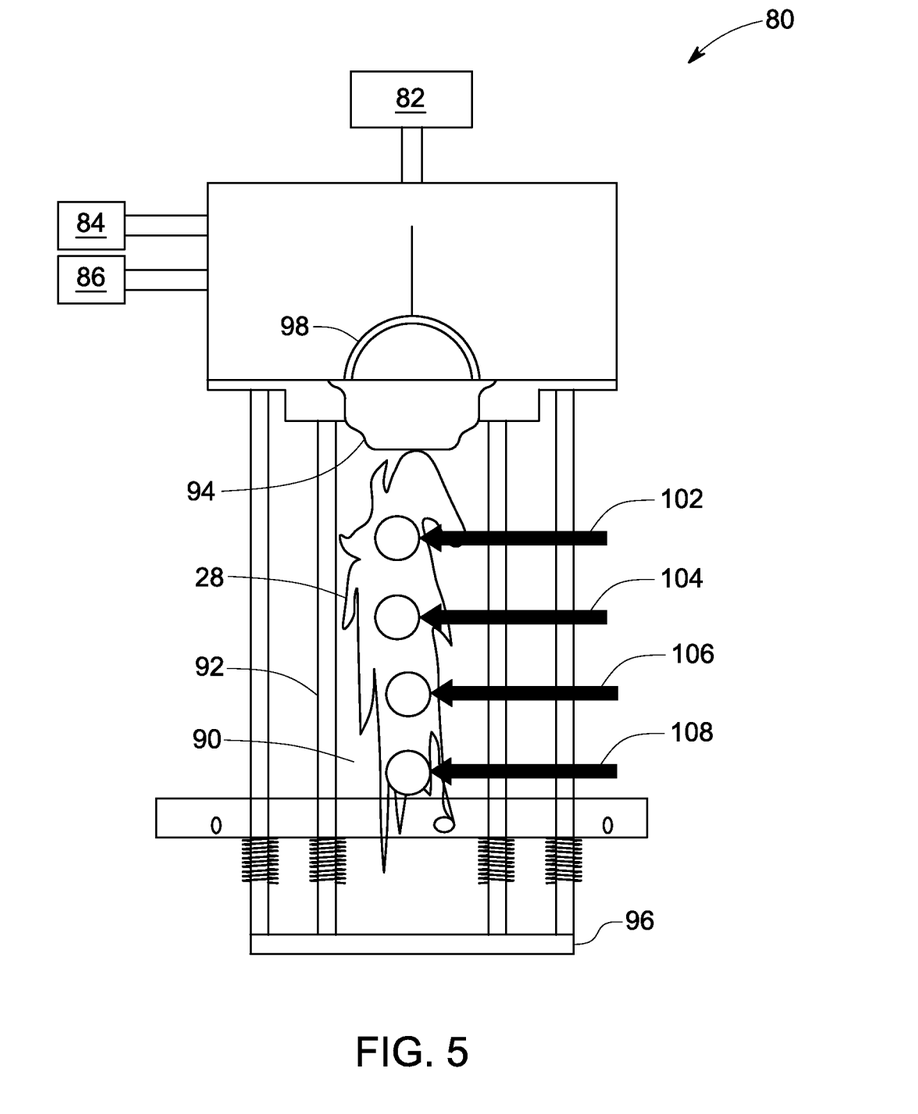
FIG. 5 is an experimental set up in accordance with one embodiment of the invention.
Figure 6:
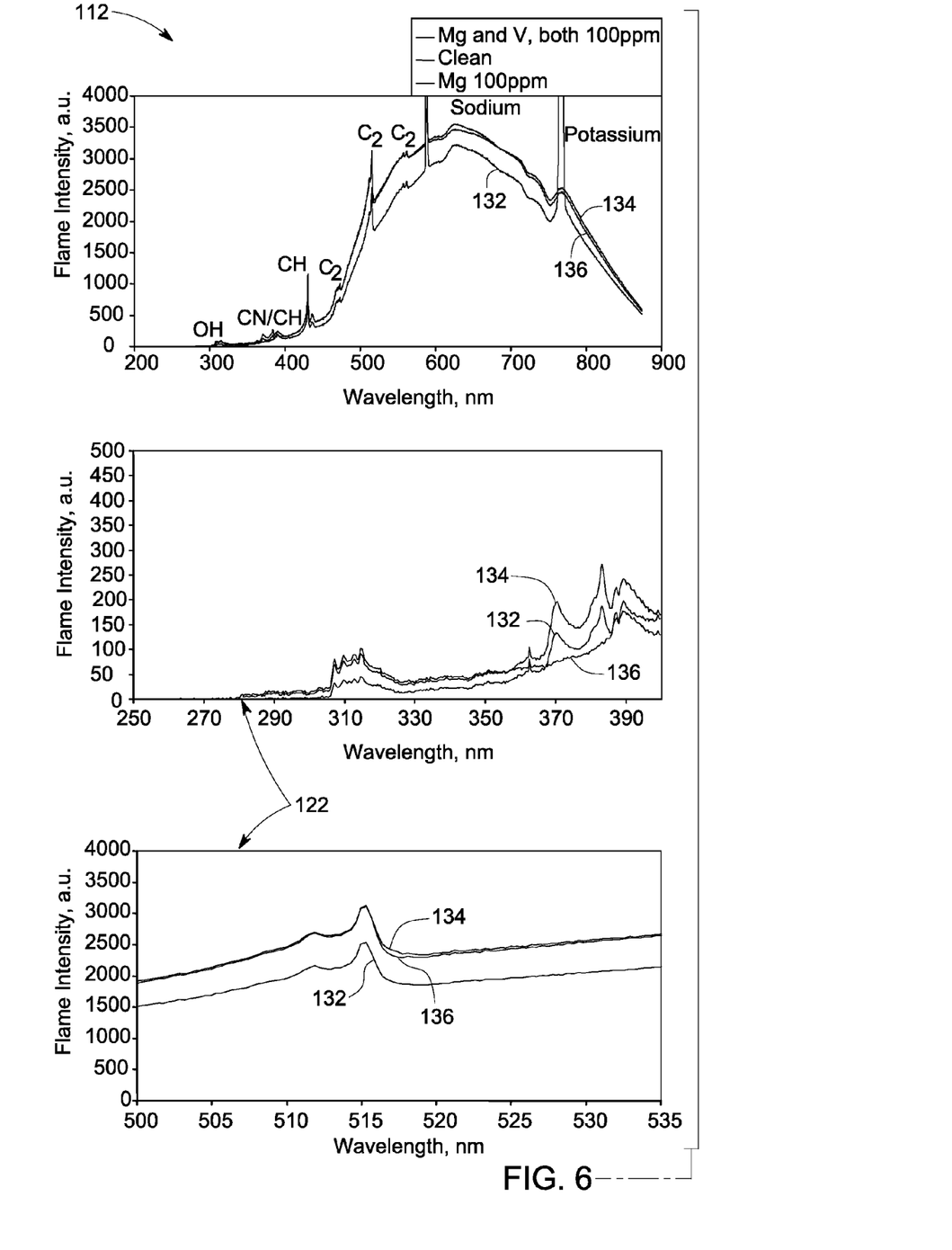
FIG. 6 is comparative flame emission spectra of magnesium and vanadium at the "nozzle end zone" of the flame in accordance with one embodiment of the invention.
Figure 7:
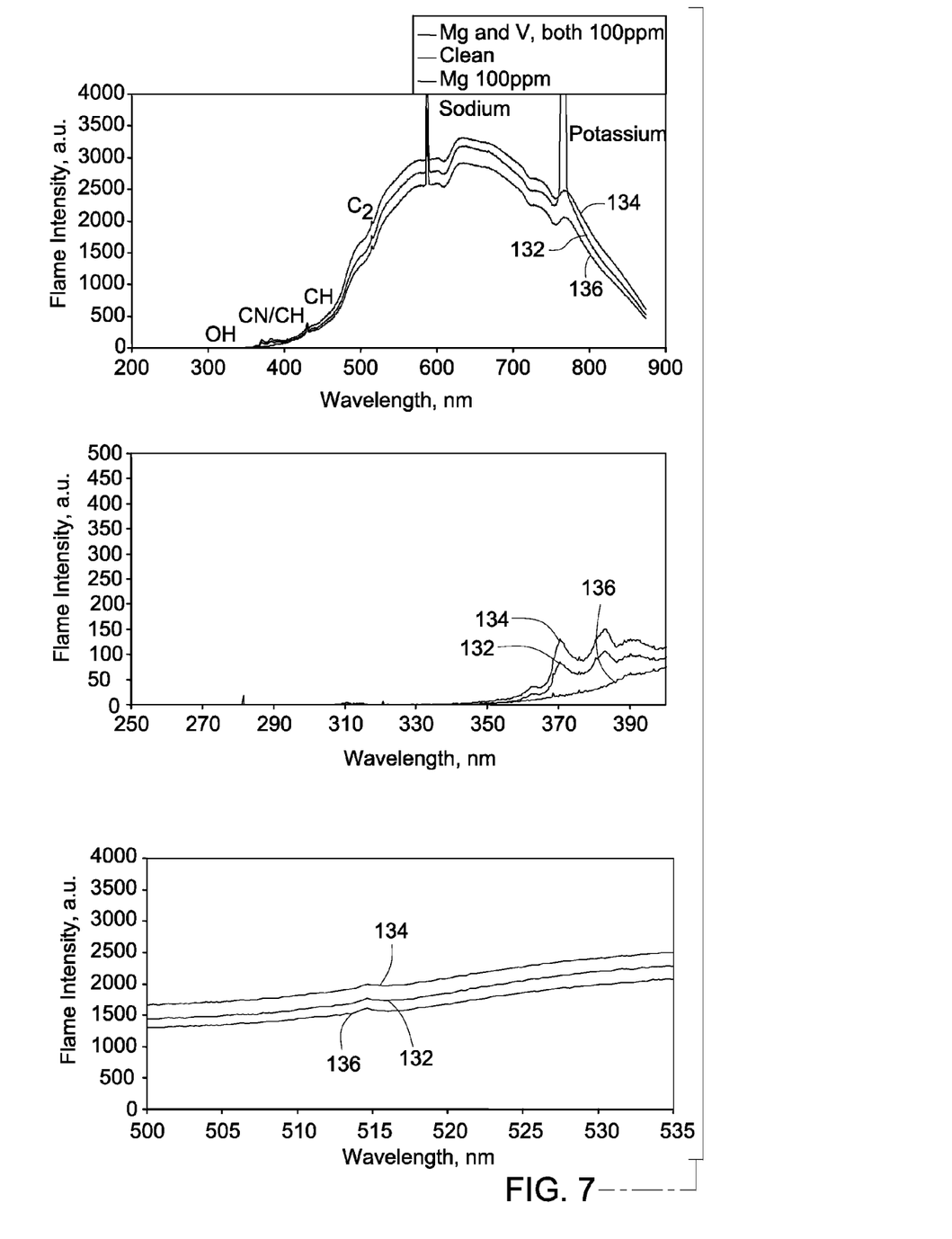
FIG. 7 is comparative flame emission spectra of magnesium and vanadium at the "mid flame zone" in accordance with one embodiment of the invention.
Figure 8:
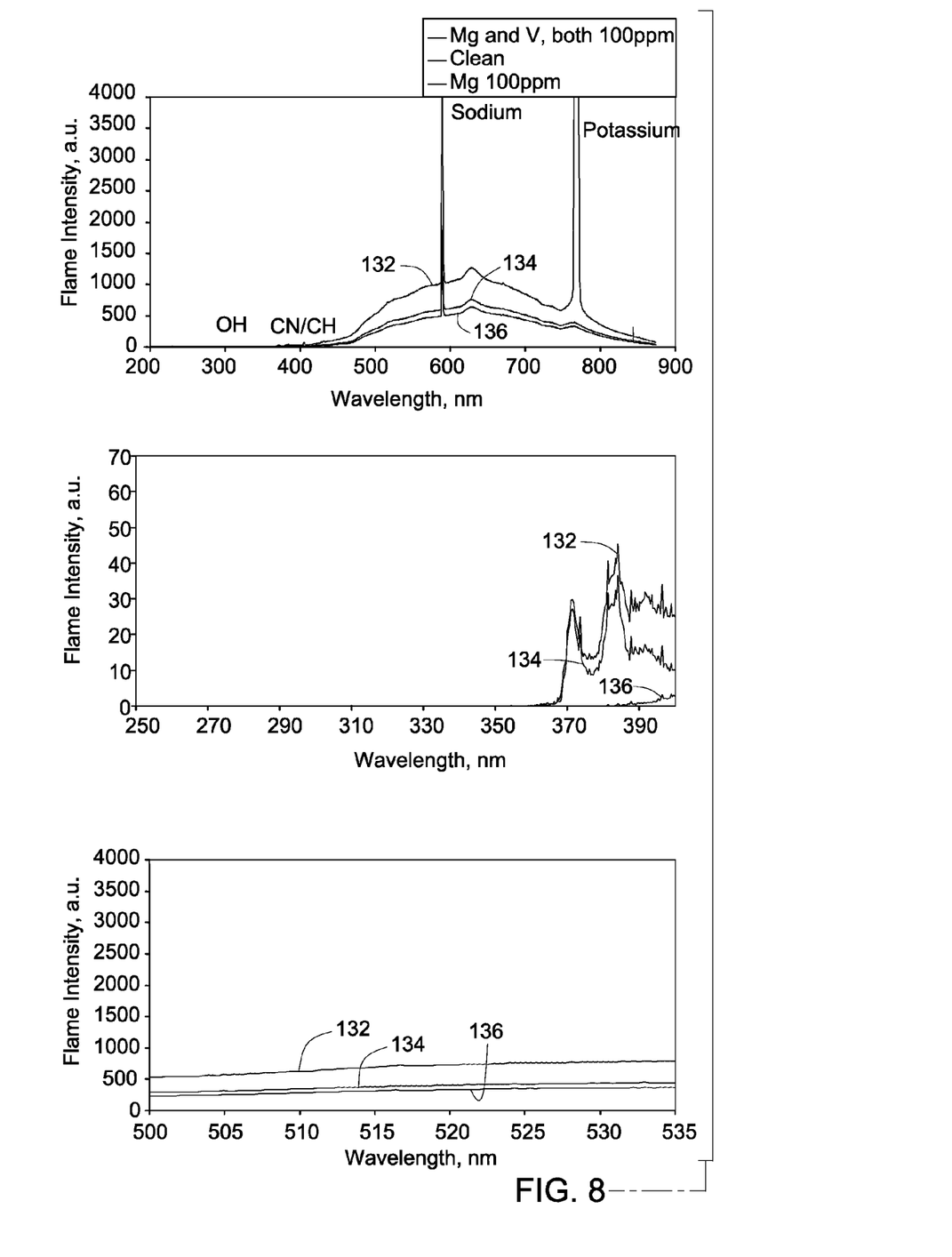
FIG. 8 is comparative flame emission spectra of magnesium and vanadium at the "tip of the end zone" of the flame in accordance with one embodiment of the invention.
Figure 9:
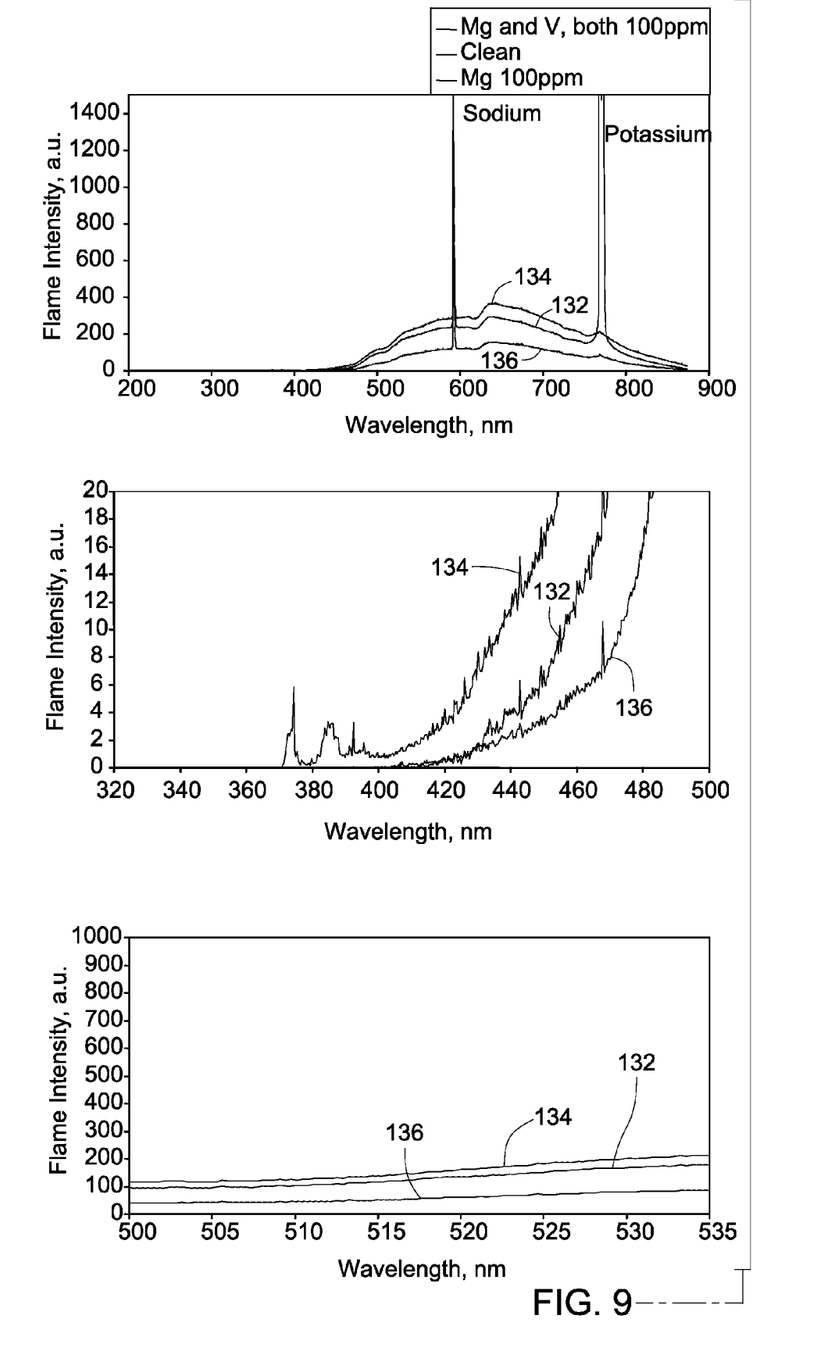
FIG. 9 is comparative flame emission spectra of magnesium and vanadium at the "downstream zone" of the flame in accordance with one embodiment of the invention.

An experimental system 80 was set up as shown in FIG. 5 to evaluate the feasibility of liquid fuel impurity detection by optical flame spectroscopy. Atmospheric pressure combustion experiments with preheated air were conducted using liquid fuels with different impurity levels. An air compressor 82 supplied preheated combustion air, and a natural gas compressor 84 supplied natural gas. Liquid fuel was supplied from a pressurized liquid dispensing tank 86. The dispensing tank was pressurized with nitrogen from a gas cylinder (not shown in the figure).

The test rig was arranged vertically as illustrated in FIG. 5 with the gases flowing downward from the exit of the test apparatus. The combustion section 90 was composed of a quartz tube 92, permitting visual access to the fuel nozzle 94 and combustion process. The quartz tubes ranged from 15 inches to 20 inches in length and were 4.92 inches in diameter. Emission measurements were made using an 8-port exhaust probe 96. The probe 96 measured area-averaged emissions, without performing any radial traverse across the combustion liner. Lighting the flame was achieved by use of a hydrogen torch 98 lit by a spark. System temperatures, flow meter pressures, flows, nozzle pressure drops, flame temperatures, and emissions were monitored by data acquisition software in concert with a data collection device (not shown in the figure).

For the combustion experiment, diesel was used as the fuel, and test runs of clean diesel, diesel with magnesium (Mg), and diesel with magnesium and vanadium (V) were obtained at 3000° F. and 3300° F. temperature. Independent analysis of the used clean diesel by an external laboratory showed levels of sodium, nickel, and vanadium to be below detectable limits. Specifically, the levels of vanadium and nickel were below 3 parts per million meters (ppmm) and level of sodium was below 5 ppmm. Fuels were decanted into polyethylene containers mounted inside a steel pressure vessel for delivery into the system.

To obtain fuel with the desired level of contaminant, oil-soluble organometallic standards were weighed out into 20 mL vials in quantities of hundreds of parts per billion (ppb) or higher using an analytical balance and quantitatively transferred by pipette into a known mass of diesel fuel contained in a cleaned two liter glass container. The fuel was shaken until homogenous. In the case of the vanadium-laden fuel, some separation was observed after a few days, but manual agitation quickly re-homogenized the mixture.

An optical flame spectrum acquisition setup (not shown in the figure), comprising several optical collimator ports, USB-spectrometers and a computer, was used to acquire optical spectra of the flame produced in the atmospheric pressure combustion test rig 80. Optical collimators were mounted on the test rig and adjusted to collect light emitted from different portions of the flame. Fiber optic cables were used to collect and transmit collected light to the compact USB spectrometers. Computer controlled fiber optic spectrometers stored captured optical spectra. An additional high-resolution spectrometer (0.02 nm resolution) was added to acquire high-resolution spectrum from the nozzle-edge part of the flame. A 518 nm narrow band-pass filter, specifically tuned to the brightest Mg emission line was introduced as an optical filter.

Four different spectra each from different portions of the flame were collected for each flame. Flame emission spectra 112, 114, 116, 118 obtained from nozzle-edge zone 102, mid flame zone 104, tip of the flame zone 106, and downstream zone 108 respectively are shown in FIG. 6-9 along with their respective high resolution spectra 122, 124, 126, 128. For all four parts of the flame, additional Mg-related emission peaks were detected when spectra 132 related to both 100 ppm Mg and 100 pm V and spectra 134 related to only 100 ppm Mg were compared to the emission spectra 136 obtained from flame of the clean diesel fuel. These peaks were identified as an atomic Mg emission line at 384 nm and magnesium oxide (Mg—O) emission line at 372 nm. A weak peak at 518 nm was observed at the "nozzle edge zone" 112. This peak was not detected for other locations. Emission spectra 132 of the fuel contaminated with both 100 ppm Mg and 100 pm V did look very similar to an emission spectra 134 of the flame produced by fuel contaminated only with 100 ppm Mg in all locations except the "Downstream zone" 116. In this location the optical spectrum of vanadium contaminated fuel showed an absence of Mg-related peaks. This phenomenon is attributed to the disappearance of atomic Mg and Mg—O from flame species by reacting with V. In this respect, Mg emission may be used to indirectly detect the presence of V, when flame emission of different portions of the flame are interrogated and compared. Therefore, with the detection of Mg and Mg—O, a method to deduce the presence of vanadium may be made possible without the direct detection of vanadium.

The embodiments described herein are examples of systems and methods having elements corresponding to the elements of the invention recited in the claims. This written description may enable those of ordinary skill in the art to make and use embodiments having alternative elements that likewise correspond to the elements of the invention recited in the claims. The scope of the invention thus includes systems and methods that do not differ from the literal language of the claims, and further includes other articles, systems and methods with insubstantial differences from the literal language of the claims. While only certain features and embodiments have been illustrated and described herein, many modifications and changes may occur to one of ordinary skill in the relevant art. The appended claims cover all such modifications and changes.

The invention claimed is:

1. A combustor system, comprising:
an up-stream fuel injection point;
a down-stream turbine combustor;
a flame zone in the turbine combustor comprising a plurality of axial sub-zones;
an optical port assembly comprising a plurality of optical ports and configured to obtain a non-axial, direct, optical view of at least two of the plurality of axial sub-zones, wherein at least one of the plurality of optical ports is aligned to have an oblique angle view of the flame zone; and
an impurity detection system in optical communication with the optical port assembly.

2. The system of claim 1, wherein at least one of the plurality of optical ports is aligned to have a radial view of the flame zone.

3. The system of claim 1, wherein the optical port assembly has an alterable view of the flame zone.

4. The system of claim 1, wherein the impurity detection system is configured to detect impurity species comprising at least one element selected from the group consisting of sodium, potassium, calcium, lithium, magnesium, lead, and vanadium.

5. The system of claim 4, wherein the impurity detection system is configured to directly detect impurity species comprising at least one element selected from the group consisting of magnesium, lead, and vanadium.

6. The system of claim 4, wherein the impurity detection system is configured to indirectly detect the impurity species of vanadium through the detection of element and oxide of magnesium.

7. The system of claim 1, wherein the impurity detection system is configured to detect impurity species comprising at least one oxide of the element selected from the group consisting of sodium, potassium, calcium, lithium, magnesium, lead, and vanadium.

8. The system of claim 7, wherein the impurity detection system is configured to directly detect a peak corresponding to the oxide of magnesium.

9. The system of claim 1, wherein the impurity detection system comprises a sensor assembly.

10. The system of claim 9, wherein the sensor assembly comprises an avalanche photodiode (APD).

11. The system of claim 9, wherein the impurity detector system further comprises a filter assembly configured to selectively allow passage of a characteristic thermal atomic emission of an impurity existing in a fuel in the turbine combustor.

12. The system of claim 11, wherein the filter assembly comprises a dielectric material.

13. The system of claim 11, wherein the filter assembly comprises a rare earth doped glass.

14. The system of claim 9, wherein the impurity detector system further comprises an analyzer assembly configured to analyze an output signal from the sensor assembly.

15. The system of claim 9, wherein the impurity detector system further comprises a photomultiplier tube (PMT) with a quantum efficiency greater than 10% at an incident wavelength of range of 300 to 700 nm.

16. The system of claim 1, wherein the system further comprises an optical fiber in communication with the optical port assembly and the impurity detection system.

17. The system of claim 1, further comprising an exciter assembly disposed to increase the temperature of the flame zone.

18. The system of claim 17, wherein the exciter assembly comprises an electrode assembly.

19. The system of claim 18, wherein the electrode assembly is configured to produce a plasma discharge.

20. The system of claim 18, wherein the electrode assembly comprises an RF coil.

21. A combustor system, comprising:
an up-stream fuel injection point;
a down-stream turbine combustor;
a flame zone in the turbine combustor comprising a plurality of axial sub-zones;
an electrode assembly disposed at the vicinity of combustor system to excite the flame during operation;
an optical port assembly comprising a plurality of optical ports and configured to obtain a direct optical view of at least two of the plurality of axial sub-zones, wherein at least one of the plurality of optical ports is aligned to have an oblique angle view of the flame zone; and
an impurity detection system in optical communication with the optical port assembly.

22. A method of analyzing and measuring specific impurities in a combustor system, comprising:
injecting a liquid fuel into a flame zone of the combustor system,
generating a flame in the flame zone of the combustor system,
increasing temperature of the flame by providing an external stimulation,
coupling a direct emission signal of the flame from a plurality of axial subzones of the flame zone through an optical port assembly to a detector system, and
analyzing the emission signal from the plurality of axial subzones to detect an impurity species present in the liquid fuel, wherein the optical port assembly comprises a plurality of optical ports and wherein at least one of the plurality of optical ports is aligned to have an oblique angle view of the flame zone.

23. The method of claim 22, wherein the impurity species comprises at least one element selected from the group consisting of sodium, potassium, calcium, lithium, magnesium, lead, and vanadium.

24. The method of claim 23, wherein the impurity species comprises at least one oxide of the element selected from the group consisting of sodium, potassium, calcium, lithium, magnesium, lead, and vanadium.

25. The method of claim 24, wherein detecting an impurity species includes comparison of different peak intensity bandwidths of the impurity species.

\* \* \* \* \*